United States Patent
Hurrey et al.

(10) Patent No.: US 11,672,863 B2
(45) Date of Patent: Jun. 13, 2023

(54) ENHANCED SOLUBILITY DRUG-CONTAINING FORMULATIONS

(71) Applicant: United Therapeutics Corporation, Silver Spring, MD (US)

(72) Inventors: Michael Laird Hurrey, San Ramon, CA (US); Drazen Ostovic, Redwood City, CA (US); Peter Noymer, Los Gatos, CA (US)

(73) Assignee: United Therapeutics Corporation, Silver Spring, MD (US)

( * ) Notice: Subject to any disclaimer, the term of this patent is extended or adjusted under 35 U.S.C. 154(b) by 103 days.

(21) Appl. No.: 16/609,544

(22) PCT Filed: May 10, 2018

(86) PCT No.: PCT/IL2018/050511
§ 371 (c)(1),
(2) Date: Oct. 30, 2019

(87) PCT Pub. No.: WO2018/207188
PCT Pub. Date: Nov. 15, 2018

(65) Prior Publication Data
US 2020/0054754 A1     Feb. 20, 2020

Related U.S. Application Data

(60) Provisional application No. 62/504,546, filed on May 11, 2017.

(51) Int. Cl.
| | |
|---|---|
| *A61K 47/12* | (2006.01) |
| *A61K 47/02* | (2006.01) |
| *A61P 23/02* | (2006.01) |
| *A61K 31/445* | (2006.01) |
| *A61K 9/00* | (2006.01) |

(52) U.S. Cl.
CPC ............ *A61K 47/12* (2013.01); *A61K 31/445* (2013.01); *A61K 47/02* (2013.01); *A61P 23/02* (2018.01); *A61K 9/0019* (2013.01)

(58) Field of Classification Search
CPC ...... A61K 31/445; A61K 47/02; A61K 47/12; A61K 9/0019; A61K 9/08; A61P 23/02
See application file for complete search history.

(56) References Cited

U.S. PATENT DOCUMENTS

| | | |
|---|---|---|
| 5,747,060 A | 5/1998 | Sackler et al. |
| 5,922,340 A | 7/1999 | Berde et al. |
| 6,045,824 A * | 4/2000 | Kim ............. A61K 9/1277 424/450 |
| 2018/0256554 A1 * | 9/2018 | Kikuchi ........ A61P 31/00 |

FOREIGN PATENT DOCUMENTS

| | | | | |
|---|---|---|---|---|
| JP | WO 2017/082121 | * | 5/2017 | ............ A61K 47/36 |
| WO | 99/13865 A1 | | 3/1999 | |
| WO | 2018/207188 A1 | | 11/2018 | |

OTHER PUBLICATIONS

International Search Report and Written Opinion for PCT/IL2018/050511 dated Oct. 4, 2018, all pages.

* cited by examiner

*Primary Examiner* — Anna R Falkowitz
(74) *Attorney, Agent, or Firm* — Foley & Lardner LLP

(57) ABSTRACT

This invention describes compositions comprising at least 75 mg/mL of solubilized otherwise poorly soluble drug in an aqueous environment, wherein the composition further comprises a combination of 3 or more acids. Methods of providing analgesia, anti-pyretic effects or reducing pain in a subject presenting with a pain condition, and methods of reducing administration site irritation, inflammation or a combination thereof in a subject presenting with a pain condition, comprising the steps of administering such compositions and infusion pumps containing such compositions are also described.

24 Claims, 1 Drawing Sheet

ENHANCED SOLUBILITY DRUG-CONTAINING FORMULATIONS

CROSS REFERENCE TO RELATED APPLICATIONS

This application is a U.S. National Phase of PCT Patent Application No. PCT/IL2018/050511 filed on May 10, 2018, which claims the benefit of U.S. Provisional Patent Application No. 62/504,546, filed on May 11, 2017, the entire contents of each of these applications is incorporated in their entirety by reference herein for all purposes.

BACKGROUND OF THE INVENTION

Solubility is defined as the concentration of the solute in a saturated solution. The solubility of compounds varies in accordance with factors such as temperature, the type of solvent, the pH of the solution, and atmospheric pressure. The solubility of drugs found in the US Pharmacopeia is expressed as the number of milliliters of solvent in which one gram of solute can dissolve. Solubility may also be expressed in terms of molarity, percentage, and molality. Typically, drugs defined as "poorly soluble" are those that require more than 1 ml part of solvent per 10 mg of solute. Some poorly soluble drugs are further limited by their intrinsic bioavailability for example due to extensive first pass metabolism by the liver (first pass effect), or further limited due to various drug-drug interactions.

Usage of poorly soluble compounds as active pharmaceutical ingredients has increased. There are several different approaches to solve the problem of solubility of poorly soluble drugs. These include traditional solubilizing approaches using a combination of solvents, surfactants and co-solvents, various sophisticated dispersion systems, as well as novel technologies, including micronization, complexation and liposomal delivery.

Pain is a symptom of many types of trauma or illness and occurs frequently following medical procedures. Many anesthetics are liposome- or aqueous-based solutions.

Previous anesthetic formulations, although useful, have several drawbacks that have rendered their use less than optimal. For example, with some topical local anesthetics, these drawbacks included limited efficacy if applied to intact skin, reduced efficacy if an excipient had been used to increase the solubility and stability of the anesthetic, the rapid decomposition of anesthetics (particularly amino-ester derived anesthetics such as tetracaine) in aqueous formulations (Smith G. G., Kennedy D. R., Nairn J. G., J. Pharm. Sci. (1974) 63 (5): 712-6. Schreier, S., Do Amaral, A. T., Stachissini, A. S., Bianconi, M. L. B., Magn. Reson. (1986) 8 (3.4): 166-71), and the slow release of anesthetics from lipophilic vehicles (Campbell, D. and Adriani, J., JAMA (1956) 162: 527-520).

Bupivacaine and Ropivacaine are anaesthetic agents with low water solubility in their freebase forms. Therefore, existing parenteral formulations of bupivacaine comprise the HCl salt hydrate or as the freebase encapsulated in liposomes. The liposomal formulation comprises bupivacaine at a concentration of 13.3 mg/mL and the HCL salt formulation is supplied as 7.5, 5 and 2.5 mg/mL solutions. Existing parenteral formulations of ropivacaine comprise the HCl salt hydrate supplied as 10, 5, and 2 mg/mL solutions.

Certain therapeutic applications of these drugs require pumps for continuous infusion, such as peripheral nerve blocks for post-surgical pain management. In these types of therapeutic applications, patients are required to carry an infusion pump around the clock. With low concentration solutions, a very large volume of infusate fluid is required each day to deliver an efficacious dose of medication, and therefore the infusion pumps for these applications are very large and cumbersome. Because of this, it is advantageous for patients to be able to administer local anesthetics via smaller ambulatory pumps or convenient patch pump devices. As a result, more highly concentrated formulations of bupivacaine and ropivacaine are highly desirable in order to ensure that the delivered dose, even in a small volume, is also efficacious.

Because both ropivacaine and bupivacaine are basic molecules, lowering the pH of the formulation to obtain various salt forms can have the desired effect of increasing the drug solubility in aqueous media.

The solubility of bupivacaine hydrochloride monohydrate has been reported to be 40-50 mg/mL in water between pH 1.8 and 6. (pH-Dependent Solubility and Dissolution of Bupivacaine and its Relevance to the Formulation of a Controlled Release System, Jaymin Shah and Manoj Maniar Journal of Controlled Release 23(3) 261-270 March 1993). Ropivacaine hydrochloride monohydrate has a solubility in water of 53.8 mg/mL (Drug description: Naropin, www.rxlist.com/naropin-drug.htm).

Traditional methods of increasing the solubility of basic drugs by employing acidic aqueous media, however, has drawbacks. First, not all salts are very water soluble, so it is not certain that a certain degree of solubility can be obtained. Second, if the buffering capacity of the resulting acidic formulation is high, local injection site irritation is more likely.

In light of the drawbacks of these prior formulations, there is therefore a need for a parenteral formulation without the adverse issues associated with existing technologies.

SUMMARY OF THE INVENTION

It is an object of this invention to provide a more concentrated formulation of free-base, poorly soluble drugs. It is another object of this invention to provide such formulation, without need for preservatives, stabilizers or lipid excipients.

It is still a further object of this invention to provide such formulation as suitable for use in limited volumes.

In some aspects of this invention, there is provided a method of providing a free-base poorly soluble drug in a formulation with improved solubility and reduced, local injection site irritation.

In some embodiments, this invention provides a composition comprising a poorly soluble drug in a formulation comprising a combination of three or more acids whereby the resulting composition is a stable aqueous formulation comprising 100 mg/mL or more of the drug.

In some aspects, such composition incorporates poorly soluble free-base anesthetics, which in some embodiments, comprise bupivacaine and ropivacaine.

This invention provides a composition comprising a free-base, poorly soluble drug in a formulation with improved solubility at a high concentration, in a small volume.

In some aspects, contrary to prior suggestion that ideal analgesia is provided by low concentrations in sustained delivery volumes over time for direct injection to nervous tissue, in one aspect, the invention provides for enhanced solubility formulations of the free-base poorly soluble analgesic administered into a nerve at a joint directly.

In some aspects, the formulations of this invention possess a pH more neutral than known formulations (ranging in some embodiments, from 5-5.5, or in some embodiments, from 5.2-5.5, or in some embodiments, from 5.3-5.5, or in some embodiments, from 5.4-5.5, or in some embodiments, being about 5.5, which in some embodiments, reduces negative effects/impact to the thus treated nerve tissue.

This invention provides a composition comprising at least 100 mg/mL of solubilized otherwise poorly soluble drug in an aqueous environment further comprising a combination of 3 or more acids.

According to this aspect, and in some embodiments, the combination of 3 or more acids is selected from the group consisting of acetic, phosphoric, hydrochloric and sulfuric acids, in any combination or combinations. According to this aspect, and in some embodiments, the combination of 3 or more acids is selected from the group consisting of acetic, phosphoric, hydrochloric, sulfuric, citric acids, in any combination or combinations.

In some embodiments, this invention provides a composition comprising at least 100 mg/mL of solubilized otherwise poorly soluble drug in an aqueous environment further comprising a combination of acids, whereby there are sufficient acidic interactions in solution to increase solubility with a concentration of each acid being below the solubility product constant (Ksp) value for the resulting salt.

In some embodiments, this invention provides a composition comprising at least 100 mg/mL of solubilized otherwise poorly soluble drug in an aqueous environment further comprising a combination of acids, whereby a combination of acids of both weak and strong acid is incorporated therein.

According to this aspect, and in some embodiments, the otherwise poorly soluble drug is in free-base form.

According to this aspect and in some embodiments, the weak acid/s will be characterized by a pKa value at least 2 less than the pKa of the poorly soluble drug, and the strong acids are characterized by a pKa value, at least 2 less than the pKa of the weak acids.

According to this aspect and in some embodiments, the strong acid will be selected from the group consisting of hydrochloric, hydrobromic, nitric, sulfuric, methanesulfonic, ethanesulfonic, benzenesulfonic or toluenesulfonic acid.

According to this aspect, and in some embodiments, the combination of 3 or more acids provides for each in a ratio that can be 1:1:1 or a different ratio.

According to this aspect, and in some embodiments, the at least 3 acids comprise at least two strong acids and one weak acid, or in some embodiments, where the ratio of strong to weak acids is present in excess of at least 2:1.

According to this aspect, and in some embodiments, the combination of 3 or more acids provides for 4 acids, in a 6:1:1:2 molar ratio of sulfuric:acetic:phosphoric:hydrochloric acid and in some embodiments, the two strong acids incorporated do not include the same acid. According to this aspect, and in some embodiments, the combination of 3 or more acids provides for 4 acids, in a 6:1:1:2 molar ratio of strong:weak:weak:strong acid, whereby the strong acids are selected from the group consisting of hydrochloric, hydrobromic, nitric, sulfuric, methanesulfonic, ethanesulfonic, benzenesulfonic or toluenesulfonic acid, or others, as are known in the art, and in some embodiments, the two strong acids incorporated do not include the same acid.

In some embodiments, the choice of strong acids incorporated will in turn alter the ratio, such that the overall ratio will still favor the presence of strong acid in excess of that of weak acids, however, the molar ration may be a 5:1:1:3 molar ratio of strong:weak:weak:strong acid, or in some embodiments, the molar ration may be a 4:1:1:4 molar ratio of strong:weak:weak:strong acid, or in some embodiments, the molar ration may be a 3:1:1:5 molar ratio of strong:weak:weak:strong acid, or in some embodiments, the molar ration may be a 6:1:1:2 molar ratio of strong:weak:weak:strong acid, where the two strong acids incorporated do not include the same acid.

In some embodiments, the combination of 3 or more acids provides for 3 acids, in a ratio of 1:2 or 2:1 of weak acid to strong acid.

In some embodiments, the molar ratio of otherwise poorly soluble drug:total acid ratio is 1.5:1, wherein other embodiments the ratio is >1:1.

According to this aspect, and in some embodiments, the composition is provided in a volume of 0.1-10 mL. According to this aspect, and in some embodiments, the composition is provided in a volume not to exceed 5-10 mL.

According to this aspect, and in some embodiments, the poorly soluble drug is an anesthetic.

According to this aspect, and in some embodiments, the otherwise poorly soluble drug is bupivacaine, ropivacaine, mepivacaine, levobupivacaine, procaine, chloroprocaine, etidocaine, prilocaine or tetracaine.

According to this aspect, and in some embodiments, the otherwise poorly soluble drug is bupivacaine or ropivacaine.

According to this aspect, and in some embodiments, the composition is preservative-free, excipient free or a combination thereof.

In some embodiments, this invention provides a method of providing analgesia, anti-pyretic effects or reducing pain in a subject presenting with a pain condition, comprising the steps of: administering a composition as herein described.

In some embodiments, this invention provides a method of reducing administration site irritation, inflammation or a combination thereof in a subject presenting with a pain condition, comprising the steps of: administering a composition as herein described.

According to this aspect, and in some embodiments, the method makes use of a selectively activatable body-worn infusion-pump assembly. According to this aspect, and in some embodiments, the infusion-pump assembly comprises said composition formulated for single use delivery in a volume not to exceed 10 mL.

In some embodiments, this invention provides a drug infusion pump loaded with a composition as herein described.

DETAILED DESCRIPTION OF THE INVENTION

Figure 1:
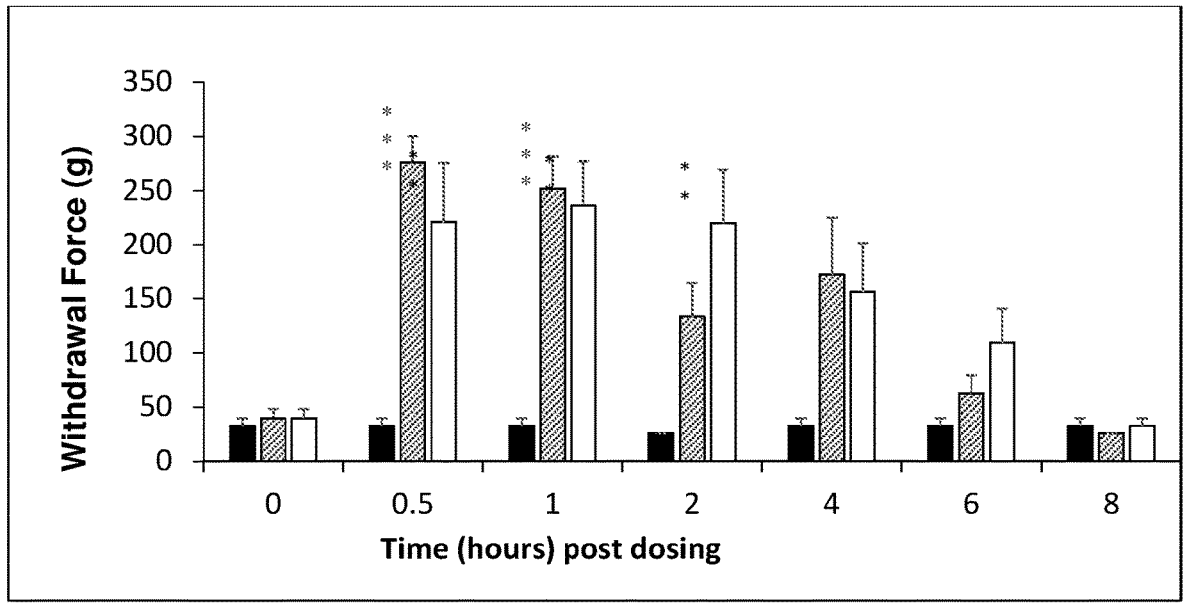
FIG. 1 plots the results of Von Frey filament testing of animal subjects, where the saline treated group is represented by the black bars, subjects treated with an embodied formulation of this invention of Bupivacaine represented by the hatched bars, and subjects treated with the marketed formulation of Bupivacaine represented by the white bars. Both Bupivacaine-containing formulations exhibit comparable magnitude of effect and duration of effect of analgesia, as compared to controls.

This invention aims to provide treatment with free-base poorly soluble drugs for patients in need of same, which is delivered in smaller volumes than existing formulations of the same drug, and in some embodiments, providing for reduced adverse effects than seen to date in subjects receiving alternate formulations of the same drug.

In some embodiments, the free-base poorly soluble drug is formulated for delivery of a comparable dosage in significantly reduced volume, as compared to alternate formulations of the same drug, where no additional excipients are included in the formulation.

Surprisingly, the instant formulations as compared to existing formulations containing the same free-base poorly soluble drugs in terms of dose (in mg/hr) providing for comparable efficacy, while significantly exceeding the known solubility limit for the stated drug.

Such enhanced solubility, in turn, facilitates the use of smaller pumping systems to administer the free-base poorly soluble drug.

In some aspects, existing solubility limitations necessitate use of large balloons pumps that can range in size to 400-500 mL, in order to achieve an effective dose. The formulations of this invention provide for reduction in the pump size by more 95%.

In some embodiments, the formulations of this invention provide for more appropriate pediatric formulations, with lower daily delivery volumes and ease of administration of lower dosages, as needed, as will be appreciated by the skilled artisan.

This invention provides a composition comprising a formerly poorly soluble drug now in solubilized form in a formulation, which in some aspects comprises a combination of acetic, phosphoric, hydrochloric and sulfuric acids whereby the resulting composition is a stable aqueous formulation comprising 100 mg/mL or more of the solubilized drug. In some aspects, such composition incorporates poorly soluble free-base containing drug, such as anesthetics, which in some embodiments, comprise bupivacaine and ropivacaine.

This invention provides a composition comprising a poorly soluble drug in a formulation with improved solubility at a high concentration, in a small volume.

In some embodiments, this invention provides a composition comprising a poorly soluble analgesic in a formulation with improved solubility at a high concentration, in a small volume.

In some aspects, contrary to prior suggestion that ideal analgesia is provided by low concentrations in sustained delivery volumes over time for direct injection to nervous tissue, in one aspect, the invention provides for enhanced solubility formulations of the free-base poorly soluble analgesic administered into a nerve at a joint directly.

In some aspects, the formulations of this invention possess a pH more neutral than known formulations (ranging in some embodiments, from 5-5.5, or in some embodiments, from 5.2-5.5, or in some embodiments, from 5.3-5.5, or in some embodiments, from 5.4-5.5, or in some embodiments, being about 5.5, which in some embodiments, reduces negative effects/impact to the thus treated nerve tissue.

In some aspects, the invention provides a composition comprising a poorly soluble drug possessing a solubility that is significantly higher, for example, at least double to up to or exceeding 20-times that of the solubility limit for other available formulations of the poorly soluble drug.

In some aspects, providing such poorly soluble drug-containing formulations with enhanced solubility in smaller volumes facilitates the use of smaller pumping systems to administer the drug.

In some aspects of this invention, there is provided a method of providing analgesia, anti-pyretic effects or reducing pain in a subject presenting with a pain condition, comprising the steps of: administering an anesthetic in a sterile fluid composition comprising a combination of acetic, phosphoric, hydrochloric and sulfuric acids to a subject wherein the composition comprises 100 mg/mL or more of the drug and a much smaller volume of drug is delivered to said subject via any appropriate means.

In some embodiments, the invention provides a method of reducing administration site irritation, inflammation or a combination thereof in a subject presenting with a pain condition, comprising the steps of: administering an anesthetic in a sterile fluid composition comprising a combination of acetic, phosphoric, hydrochloric and sulfuric acids to a subject, wherein the composition comprises 100 mg/mL or more of the drug and a much smaller volume of drug is delivered to said subject via any appropriate means.

In some aspects, diminishing or abrogating certain side effects may in turn lead to greater analgesic effect, as well.

In some embodiments such methods result in the ability to achieve the desired analgesic, anti-inflammatory, anti-pyretic effect or combination thereof in the patient with a much smaller volume of delivery.

In some embodiments, such method results in less of a need to administer continuous dosages over time or provide for similar or longer delivery durations in much smaller volumes over time and in some embodiments, such method results in a less frequent need for adjustment of a dosage provided to such subject, over time, and in some embodiments, such method provides for a combination of these phenomena.

In some embodiments, the formulations/compositions of the present invention provide for the ultimate delivery of complete analgesia obtained faster and in a smaller volume in a subject, than was attainable with other compositions containing the same drug.

In some embodiments, the methods make use of and compositions are formulated for an infusion-pump assembly comprising a unit dosage form comprising a poorly soluble freebase form of a drug for administration to a subject in need thereof.

In some embodiments, the poorly soluble freebase form of a drug is formulated for single use delivery in a volume not to exceed 5-10 mL.

This invention also provides a drug infusion pump loaded with an amount of a poorly soluble freebase form of a drug providing for a reduced dosage than typically provided, wherein said drug is in a sterile fluid composition and said drug is present at a concentration of between 75 mg/mL and 150 mg/mL formulated for single use delivery in a volume not to exceed 10 mL.

In some embodiments, the invention also provides a drug infusion pump loaded with an amount of ropivacaine, wherein said ropivacaine is in a sterile fluid composition and is present at a concentration of between 88-110 mg/mL formulated for single use delivery in a volume not to exceed 10 mL.

In some embodiments, the invention also provides a drug infusion pump loaded with an amount of bupivacaine, wherein said bupivacaine is in a sterile fluid composition and is present at a concentration of between 85-150 mg/mL formulated for single use delivery in a volume not to exceed 10 mL.

According to this aspect and in some embodiments, the drug infusion pump is a body-worn infusion pump and in some embodiments, the pump is a pre-filled and preprogrammed pump. In some embodiments, the drug infusion pump is preprogrammed to administer the drug according a method as herein described.

It is to be understood that the term "patch pump" as referred to herein, is to be understood to relate to any or be exchangeable with any body-worn infusion pump.

In some embodiments, the composition is at a pH of about from 5 or 5.1 to about 5.6.

In some embodiments, the drug is Bupivacaine. In some embodiments, the drug is Ropivacaine. In some embodiments, the drug is lidocaine, mepivacaine, levobupivacaine, procaine, chloroprocaine, etidocaine, prilocaine or tetracaine.

This invention provides for increasing the solubility of basic drugs by employing acidic aqueous media.

According to this aspect and in some embodiments, the invention provides compositions and methods whereby a high degree of solubility of the basic drugs can be obtained.

According to this aspect and in some embodiments, the invention provides compositions and methods, whereby local injection site irritation is reduced, as compared to other free-base drug containing compositions of the same drug.

In some aspects, the use of a combination of acetic, phosphoric, hydrochloric and sulfuric acids provides for stable aqueous formulations of, inter alia, bupivacaine and ropivacaine of over 100 mg/mL of freebase with limited buffering capacity well suited for use in patch-pumps or other continuous or pulsatile drug delivery pumps.

In some embodiments, the combination of acetic, phosphoric, hydrochloric and sulfuric acids provide for each in a 1:1:1:1 ratio.

In some embodiments, the ratio of acetic, phosphoric, hydrochloric and sulfuric acids ranges from 6:1:1:2 sulfuric:acetic:phosphoric:hydrochloric acid. In some embodiments, additional acids may be used, for example, citric, maleic acid or fumaric acid may be interchanged for the acids listed above.

In some embodiments, this invention provides a composition comprising at least 100 mg/mL of solubilized otherwise poorly soluble drug in an aqueous environment further comprising a combination of acids, whereby there are sufficient acidic interactions in solution to increase solubility with a concentration of each acid being below the Ksp value for the resulting salt.

In some embodiments, this invention provides a composition comprising at least 100 mg/mL of solubilized otherwise poorly soluble drug in an aqueous environment further comprising a combination of acids, whereby a combination of acids of both weak and strong acid is incorporated therein.

According to this aspect, and in some embodiments, the otherwise poorly soluble drug is in free-base form.

According to this aspect and in some embodiments, the weak acid/s will be characterized by a pKa value at least 2 less than the pKa of the poorly soluble drug, and the strong acids are characterized by a pKa value, at least 2 less than the pKa of the weak acids.

According to this aspect and in some embodiments, the strong acid will be selected from the group consisting of hydrochloric, hydrobromic, nitric, sulfuric, methanesulfonic, ethanesulfonic, benzenesulfonic or toluenesulfonic acid.

According to this aspect, and in some embodiments, the combination of 3 or more acids provides for each in a ratio that can be 1:1:1 or a different ratio.

According to this aspect, and in some embodiments, the at least 3 acids comprise at least two strong acids and one weak acid, or in some embodiments, where the ratio of strong to weak acids is present in excess of at least 2:1.

According to this aspect, and in some embodiments, the combination of 3 or more acids provides for 4 acids, in a 6:1:1:2 molar ratio of sulfuric:acetic:phosphoric:hydrochloric acid. According to this aspect, and in some embodiments, the combination of 3 or more acids provides for 4 acids, in a 6:1:1:2 molar ratio of strong:weak:weak:strong acid, whereby the strong acids are selected from the group consisting of hydrochloric, hydrobromic, nitric, sulfuric, methanesulfonic, ethanesulfonic, benzenesulfonic or toluenesulfonic acid, or others, as are known in the art. According to this aspect, and in some embodiments, the combination of 3 or more acids provides for 4 acids, each in a 6-1:1:1:2-1 ratio.

In some embodiments, the choice of strong acids incorporated will in turn alter the ratio, such that the overall ratio will still favor the presence of strong acid in excess of that of weak acids, however, the molar ration may be a 5:1:1:3 molar ratio of strong:weak:weak:strong acid, or in some embodiments, the molar ration may be a 4:1:1:4 molar ratio of strong:weak:weak:strong acid, or in some embodiments, the molar ration may be a 3:1:1:5 molar ratio of strong:weak:weak:strong acid, or in some embodiments, the molar ration may be a 6:1:1:2 molar ratio of strong:weak:weak:strong acid, where the two strong acids incorporated do not include the same acid.

In some embodiments, the combination of 3 or more acids provides for 3 acids, in a ratio of 1:2 or 2:1 of weak acid to strong acid.

In some embodiments, the molar ratio of otherwise poorly soluble drug:total acid ratio is 1.5:1, wherein other embodiments the ratio is >1:1.

In some aspects, the invention provides a composition whereby in situ salt formation occurs and a combination of at least 3 or more generally recognized as safe (GRAS) acids are contemplated for use in accordance with this aspect.

In some embodiments, the combination of 3 or more acids provides for 3 acids, in a ratio of 2:1, 1:1 or 1:2 of weak acid to strong acid ratio In some embodiments, the molar ratio of otherwise poorly soluble drug:total acid ratio is 1.5:1 or >1:1 ratio.

In some aspects, the composition will comprise 3 or more, or in some embodiments, four or more acids as described herein, wherein the acid is selected from the group consisting of: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (–L), salicylic acid, sebacic acid, stearic acid, succinic acid, sulfuric acid, tartaric acid (+L), thiocyanic acid, toluenesulfonic acid (p), undecylenic acid, Acid Modified Starch, Aconitic Acid, Cholic acid, Desoxycholic acid, Erythorbic acid (D-isoascorbic acid), Linoleic acid, Sorbic acid, Stearic acid, Sulfamic acid, Tannic acid (hydrolyzable gallotannins), Taurocholic acid and Thiodipropionic acid.

This invention provides for compositions and methods of use of same, whereby the formulations of this invention are preservative-free, excipient free and require no other solubilizing agents or preservatives.

In some aspects, the combination of four different acids greatly increases the solubility of the free-base poorly soluble drug, for example, such as, bupivacaine and ropivacaine, in an aqueous formulation while providing for a low buffering capacity of the acidic medium, which in some embodiments, promotes the pH of the tissue infiltrate rapidly rising to the prevailing physiological level so that administration site irritation is minimized.

In some embodiments, the formulations/compositions of the present invention comprise Bupivacaine and provide for the ultimate delivery of complete analgesia obtained faster and in a smaller volume in a subject, than was attainable with other compositions containing the same drug.

In some embodiments, the formulations/compositions of the present invention comprise Ropivacaine and provide for the ultimate delivery of complete analgesia obtained faster and in a smaller volume in a subject, than was attainable with other compositions containing the same drug.

In some embodiments, the formulations/compositions of the present invention comprise mepivacaine, levobupivacaine, procaine, chloroprocaine, etidocaine, prilocaine or tetracaine and provide for the ultimate delivery of complete analgesia obtained faster and in a smaller volume in a subject, than was attainable with other compositions containing the same respective drug.

In some embodiments, the formulation, kits, devices and methods of this invention provide for comparable efficacy obtained with other free-base drug containing compositions using lower volumes/more concentrated formulations, as compared to other compositions containing the identical free-based drug.

In some embodiments, the formulation, kits, devices and methods of this invention provide for prolonged, relatively consistent delivery of the drug in a smaller volume to a subject in need thereof, which in turn, in embodied aspects, provides for a more optimal therapeutic profile, including better analgesia to the subject, reduced side effects to the subject, more consistent delivery profiles to the subject, ease of use of drug containing delivery devices, etc.

In some aspects, this invention provides a formulation of Bupivacaine, or in some embodiments, Ropivacaine, or in some embodiments, mepivacaine, or in some embodiments, levobupivacaine, or in some embodiments, procaine, or in some embodiments, chloroprocaine, or in some embodiments, etidocaine, or in some embodiments, prilocaine or in some embodiments, tetracaine and provides for the ultimate delivery of complete analgesia obtained faster and in a smaller volume, which formulation has a maximal volume of infusion which does not exceed 10 mL. In some aspects, the delivery volume is 2 mL per day for a normal adult and in some embodiments, the delivery volume is from 1-3 mL per day. In some embodiments the delivery volume is from 0.5-5 mL per day.

In some aspects, the invention provides for a single use container comprising the described bupivacaine formulation for delivery by infusion pump, which formulation provides for fewer side effects experienced by the patient in use of same.

In some aspects, the invention provides for a single use container comprising the described Bupivacaine, or in some embodiments, Ropivacaine, or in some embodiments, mepivacaine, or in some embodiments, levobupivacaine, or in some embodiments, procaine, or in some embodiments, chloroprocaine, or in some embodiments, etidocaine, or in some embodiments, prilocaine or in some embodiments, tetracaine formulation for delivery by infusion pump in a significantly smaller delivery volume, as compared to other formulations of the identical drug in use to date.

In some embodiments, reference to the compositions, kits and methods/uses of the invention, which refer to the term "comprise" or "comprising" also encompasses "consist of" or "consisting of".

In some embodiments, the unit dosage forms, compositions, kits and methods consist essentially of the poorly soluble drug, in the described formulation, whereby the term "consist essentially of" specifically excludes an additional active ingredient with anti-pyretic, or anti-inflammatory activity. In some embodiments, the term "consist essentially of" specifically excludes an additional active ingredient with anti-oxidant activity.

In some embodiments, the term "comprise" refers to the inclusion of the indicated active agent, such as the described analgesics, as well as inclusion of other active agents, and pharmaceutically acceptable carriers, excipients, emollients, antioxidants, stabilizers, etc., as are known in the pharmaceutical industry. In some aspects, the invention specifically contemplates a composition consisting essentially of the poorly soluble drug and the indicated acidic components to solubilize same in an aqueous carrier, without need for further excipients.

"Pharmaceutical composition" or "composition" means a composition containing one or more drugs or prodrugs, and optionally one or more excipients, as well as any product which results, directly or indirectly, from combination, complexation or aggregation of any two or more of the excipients and/or the drug or prodrug, or from dissociation of one or more of the excipients and/or drug and/or prodrug, or from other types of reactions or interactions of one or more of the excipients and/or drug and/or prodrug. Accordingly, the pharmaceutical composition of the present invention encompasses any composition obtainable by admixing a carrier-linked poorly soluble drug of the present invention and a pharmaceutically acceptable excipient.

The term "excipient" refers to a diluent, adjuvant, or vehicle with which the carrier-linked poorly soluble drug is administered. Such pharmaceutical excipient can be sterile liquids, such as water and oils.

Examples of suitable pharmaceutical excipients are described in "Remington's Pharmaceutical Sciences" by E. W. Martin.

The term "pharmaceutically acceptable" means approved by a regulatory agency such as the EMA (Europe) and/or the FDA (US) and/or any other national or regional regulatory agency for use in animals, preferably in humans.

In some aspects, the amount of drug provided in a medication or kit according to the invention is sufficient to achieve the desired effect, which in some aspects, will depend on the concentration of the compound used, and the weight and condition of the patient.

In the manufacture of a medicament according to the invention, hereinafter referred to as a "formulation," the poorly soluble drug may be admixed with, inter alia, an acceptable carrier. The carrier must, of course, be acceptable in the sense of being compatible with any other ingredients in the formulation and must not be deleterious to the subject.

As will be appreciated by the skilled artisan, the terms "subject" and "patient" are used interchangeable and refer to any subject in need of or benefitting in any way from the described treatment/administration protocol/method of kit provided by the instant invention.

This invention provides, in some aspects, a selectively activatable body-worn infusion-pump assembly comprising a sealed prefilled drug-reservoir containing the unit dosage form of the poorly soluble in a sterile fluid composition formulated as herein described.

In some embodiments, the term "automatic infusion device" refers to a device that enables an individual (also referred to herein as a user or a patient or subject) to self-administer a dosage of a substance, such as a liquid medication, wherein the device differs from a standard syringe by the inclusion of a mechanism for automatically delivering the medication to the individual by infusion when the mechanism is engaged.

In some aspects, as will be appreciated by the skilled artisan, any appropriate automatic infusion device may be used, for example, as described in U.S. Pat. Nos. 3,910,260; 4,004,577; 4,689,042; 4,755,169; 4,795,433; 3,941,130; 4,261,358; 5,085,642; 5,092,843; 5,102,393; 5,267,963; 6,149,626; 6,270,479; 8,679,061 and 6,371,939, each of which is incorporated by reference herein in its entirety.

In some aspects, the invention contemplates kits comprising a container, which may include a vial, for infusion, or in some embodiments, one or more prefilled drug-reservoirs containing the drug-containing formulations as herein described. In some aspects, the kits may further comprise instructions, such as a product insert or label, directing the user regarding proper administration and use of the formulation, or in some embodiments, instructions for making use of the formulations varying, for example in terms of volume delivery provided with said kit In some embodiments, the present invention overcomes previous limitations in terms of the existing poorly soluble drug formulations, by obviating or reducing side effects, such as irritation and inflammation, or administration site pain.

In some aspects, the present invention thus provides a concentrated, stable formulation, which in some embodiments, is provided as part of a compact pump delivery system, allowing for safer and more tolerated drug delivery, with for example, safer dosing and delivery in smaller volumes than currently possible.

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXAMPLES

Preparation of Highly Concentrated Soluble Aqueous Formulations Containing Bupivacaine Example 1

Bupivacaine (10 g, freebase form) was added to a 100 mL glass vial. To the vial was added acetic acid (0.142 mL), 85% phosphoric acid (0.17 mL) and 1M HCl (5 mL), followed by water (90 mL) To this mixture, was added sulfuric acid (0.755 mL) and water (ca. 5 mL) to afford 100 mL of the mixture. The mixture was treated with additional sulfuric acid until a clear solution was obtained and the resulting solution was stirred at 25 deg. C. at 100 rpm for 24 h.

Preparation of Highly Concentrated Soluble Aqueous Formulations Containing Ropivacaine Example 2

Ropivacaine (10 g, freebase form) was added to a 100 mL glass vial. To the vial was added acetic acid (0.142 mL), 85% phosphoric acid (0.17 mL) and 1M HCl (5 mL), followed by water (90 mL) To this mixture, was added sulfuric acid (0.850 mL) and water (ca. 5 mL) to afford 100 mL of the mixture. The mixture was treated with additional sulfuric acid until a clear solution was obtained and the resulting solution was stirred at 25 deg. C. at 100 rpm for 24 h.

Table 1 depicts the properties of the obtained formulations in Examples 1 and 2.

TABLE 1

Properties of Bupivacaine- and Ropivacaine-Containing Formulations:

| | | Initial | 24 h | 48 h | 1 month |
|---|---|---|---|---|---|
| Bupivacaine | pH | 1.0 | 1.2 | 5.6 | 5.6 |
| | Solubility mg/mL | | 85.5 | 147.7 | 135.8 |
| | Purity area % | 99.9 | | | 99.9 |
| Ropivacaine | pH | 1.4 | 1.6 | 5.2 | 5.3 |
| | Solubility mg/mL | | 88.0 | 109.6 | 101.0 |
| | Purity area % | 100 | | | 99.7 |

As is evident from the Table, the pH and purity values essentially remained stable one month following the preparation.

Comparative In Vivo Efficacy of Highly Concentrated Soluble Aqueous Formulations Containing Bupivacaine Example 3

The efficacy of the novel 100 mg/mL bupivacaine formulation was tested in animals against the commercially available 5 mg/mL bupivacaine formulation sold as Marcaine®. The animal study involved three cohorts of pigs (two test cohorts and one control cohort). There were 5 pigs per cohort. Each animal in the test cohorts received a single injection of 25 mg of bupivacaine at the sciatic nerve: either as 0.25 mL of the 100 mg/mL formulation or as 5 mL of the marketed 5 mg/mL formulation. The control cohort received a single injection of 0.25 mL of saline to act as a negative control, for which no anesthetic effect should be detected.

Measurements of the anesthetic effect of the injection were taken just prior to the injection and at 0.5, 1, 2, 4, 6 and 8 hours after the injection. There were two sets of measurements taken. The first was the local tactile sensitivity on the foot, measured with Von Frey filaments and expressed as the force required to induce the pig to withdraw its foot in reaction to being poked with the filament (higher force=stronger anesthetic effect). The second was a General Behavior score intended to evaluate the degree of loss of gross motor control at the hind legs as the pigs would walk around post-injection (higher score=stronger anesthetic effect).

FIG. 1 presents the results from the testing with the Von Frey filaments. The saline group is represented by the black bars, the novel formulation by the hatched bars, and the marketed formulation by the white bars. As can be seen in the figure, the control group exhibits no anesthetic effect over the 8-hour time period. Both the novel formulation and the marketed formulation exhibit comparable magnitude of effect and duration of effect. The asterisks above the bars represent the p-value for testing statistical significance of both active formulations by ANOVA compared to the control formulation. The number of asterisks indicates the degree of statistical significance (* is $p<0.05$,  is $p<0.01$, * is $p<0.001$). In the first hour, both active formulations have a statistically significantly anesthetic effect, with the degree of significance being higher for the novel formulation. After the first hour, for both formulations, the effect begins to wear off, with no statistical or practical difference between the active formulations and the saline formulation after 8 hours.

Figure 2:
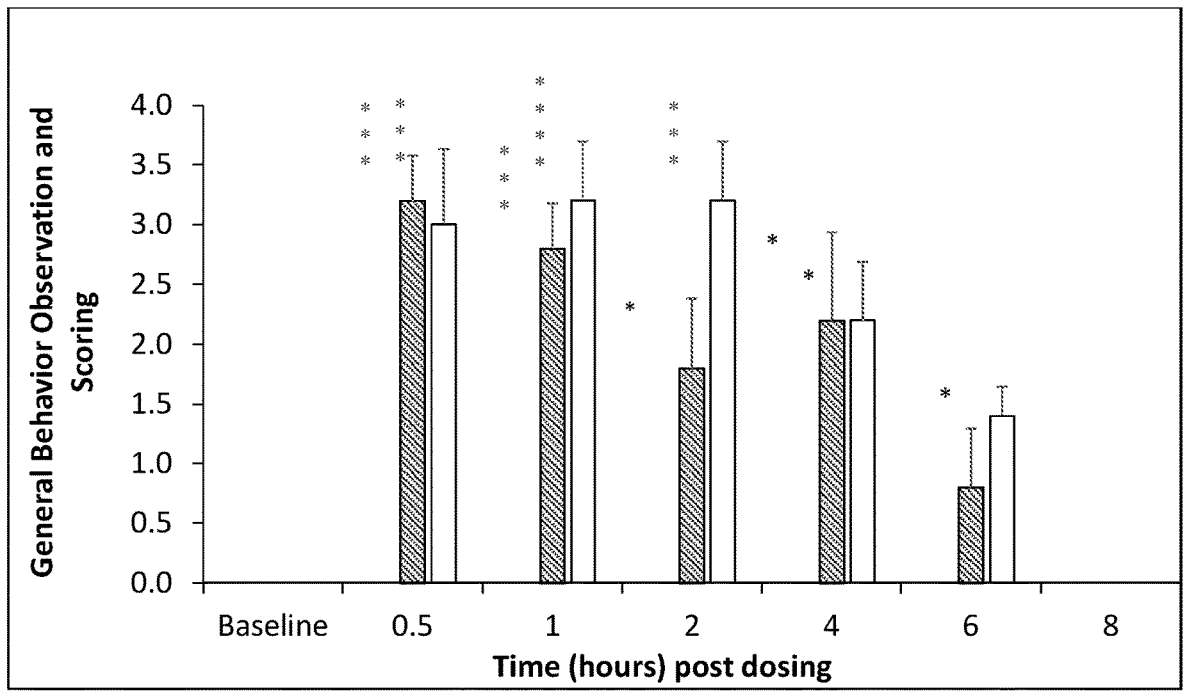
FIG. 2 plots the results of the evaluation of gross motor control in the tested animal subjects. Subjects receiving saline alone are represented by the black bars, subjects treated with an embodied formulation of this invention of Bupivacaine represented by the hatched bars, and subjects treated with the marketed formulation of Bupivacaine represented by the white bars. While the control group exhibits no effect over the 8-hour time period, as with the tactile response testing, both Bupivacaine-containing formulations exhibit comparable magnitude of effect and duration of effect of analgesia, as compared to controls.

FIG. 2 presents the results from the evaluation of gross motor control in the animal subjects. Again, the saline group is represented by the black bars, the novel formulation by the hatched bars, and the marketed formulation by the white bars. As can be seen in the figure, the control group exhibits no effect over the 8-hour time period. As with the tactile response testing, both the novel formulation and the marketed formulation exhibit comparable magnitude of effect and duration of effect. Over the first four hours, both active formulations have a statistically significantly anesthetic effect. After that, the effect begins to wear off, with no statistical or practical difference between the active formulations and the saline formulation after 8 hours.

It will be apparent to those skilled in the art that various modifications and variations can be made to the compositions and processes of this invention. Thus, it is intended that the present invention cover such modifications and variations, provided they come within the scope of the appended claims and their equivalents. The disclosure of all publications cited above is expressly incorporated herein by reference in their entirety to the same extent as if each were incorporated by reference individually.

What is claimed is:

1. A composition comprising an aqueous solution comprising drug selected from the group consisting of bupivacaine, ropivacaine, mepivacaine, levobupivacaine, procaine, chloroprocaine, etidocaine, prilocaine, and tetracaine, wherein a concentration of the drug in the aqueous solution is at least 75 mg/mL.

2. The composition of claim 1, wherein the aqueous solution is prepared by adding to said drug in a free-base form a combination of 3 or more acids.

3. The composition of claim 2, wherein each acid of said combination of 3 or more acids is selected from the group consisting of acetic, phosphoric, hydrochloric and sulfuric acids.

4. The composition of claim 2, wherein each acid of said combination of 3 or more acids is selected from the group consisting of acetic, phosphoric, hydrochloric, sulfuric, and citric acids.

5. The composition of claim 2, wherein said combination of 3 or more acids comprises a combination of four or more acids.

6. The composition of claim 5, wherein said combination of 3 or more acids is a combination of four acids.

7. The composition of claim 1, wherein said drug is an anesthetic.

8. The composition of claim 1, wherein said drug is bupivacaine or ropivacaine.

9. The composition of claim 2, wherein said drug is bupivacaine and said combination of acids consists essentially of sulfuric, acetic, phosphoric and hydrochloric acid at a 6:1:1:2 molar ratio.

10. The composition of claim 2, wherein said drug is ropivacaine and said combination of acids consists essentially of sulfuric, acetic, phosphoric and hydrochloric acid at a 6:1:1:2 molar ratio.

11. The composition of claim 1, wherein said solution has a pH of from about 5 to about 5.6.

12. The composition of claim 2, wherein said combination of 3 or more acids includes 4 acids, at a 6:1:1:2 molar ratio of sulfuric:acetic:phosphoric:hydrochloric acid ratio.

13. The composition of claim 2, wherein the combination of 3 or more acids is added to the drug at a molar ratio of the drug to the acids of between 1.5-1.

14. The composition of claim 2, wherein said combination of 3 or more acids comprises a combination of at least one strong acid and at least one weak acid.

15. The composition of claim 14, wherein the at least one weak acid has is a pKa value being at least 2 less than a pKa value of said drug.

16. The composition of claim 15, wherein the at least one strong acid has a pKa value being at least 2 less than a pKa value of said at least one weak acid.

17. The composition of claim 16, wherein the at least one strong acid is selected from the group consisting of hydrochloric, hydrobromic, nitric, sulfuric, methanesulfonic, ethanesulfonic, benzenesulfonic or toluenesulfonic acid.

18. The composition of claim 1, wherein said composition is preservative-free, excipient free or a combination thereof.

19. The composition of claim 1, wherein said solution is provided in a volume of 5-10 mL.

20. A method of providing analgesia, anti-pyretic effects or reducing pain in a subject presenting with a pain condition, comprising the steps of: administering the composition of claim 1.

21. A method of reducing administration site irritation, inflammation or a combination thereof in a subject presenting with a pain condition, comprising the steps of: administering the composition of claim 1.

22. The method of claim 20, wherein said method makes use of a selectively activatable body-worn infusion-pump assembly.

23. The method of claim 22, wherein said infusion-pump assembly comprises said composition formulated for single use delivery in a volume not to exceed 10 mL of the solution.

24. A drug infusion pump loaded with the composition of claim 1.

\* \* \* \* \*